United States Patent [19]

Dempsey

[11] Patent Number: 5,235,990

[45] Date of Patent: Aug. 17, 1993

[54] APPARATUS FOR NEUTRALIZING IRRITANTS INTRODUCED INTO A BODY VIA A BITE OR STING

[76] Inventor: Robert N. Dempsey, 4541 Wagon Wheel Rd., Carson City, Nev. 89703

[21] Appl. No.: 722,652

[22] Filed: Jun. 28, 1991

[51] Int. Cl.⁵ ............................................. A61N 1/32
[52] U.S. Cl. .................................. 607/145; 607/153
[58] Field of Search ............................... 128/800–801, 128/783, 743, 42.1, 419 R, 639, 803; 361/232

[56] References Cited

U.S. PATENT DOCUMENTS

| | | | |
|---|---|---|---|
| 2,327,874 | 8/1943 | Jong | 128/800 |
| 2,447,127 | 8/1948 | Landauer | 128/800 |
| 3,961,623 | 6/1976 | Milani et al. | 128/639 |
| 4,155,366 | 5/1979 | Di Mucci | 128/421 |
| 4,738,250 | 4/1988 | Fulkerson et al. | 128/421 |
| 4,741,347 | 5/1988 | Robert et al. | 128/800 |
| 4,873,609 | 10/1989 | Mackey | 361/232 |
| 4,951,668 | 8/1990 | Reed | 128/419 R |
| 4,982,743 | 1/1991 | Pierson | 128/800 |
| 5,074,305 | 12/1991 | Guderian | 128/783 |

OTHER PUBLICATIONS

Guderian et al., "High Voltage Shock Treatment for Snake Bite" The Lancet, Jul. 26, 1986, p. 229.

Primary Examiner—Lee S. Cohen
Assistant Examiner—Jeffrey R. Jastrzab
Attorney, Agent, or Firm—Thorpe, North & Western

[57] ABSTRACT

An apparatus for neutralizing, or reducing the effects of, irritants introduced into a subject's body by the sting or bite of an animal such as a snake, spider, or insect. Embodiments of the apparatus include a self-contained electrical power source and are compact and easy to use by a single person. A pair of electrodes are provided on the apparatus which are adapted to make electrical contact with the subject's body at the site of a sting or bite. The apparatus generates a series of pulses which are conveyed to the electrodes. The pulses have a frequency in the range from about 5 Hz to about 50 Hz and a duration in the range from about 50 microseconds to about 50 milliseconds. The intensity of the pulses is controlled and are preferably alternatively positive pulses and negative pulses to reduce problems such as electrode polarization and tissue damage. The frequency, intensity, and duty cycle of the pulses is controlled so that discomfort due to the treatment is minimized. It is preferred that the current pulses delivered to the body be in the range from about 500 microamps to about 10 milliamps. Components for measuring the current delivered to the body through the electrodes over a period of time are also provided.

21 Claims, 5 Drawing Sheets

APPARATUS FOR NEUTRALIZING IRRITANTS INTRODUCED INTO A BODY VIA A BITE OR STING

BACKGROUND

1. Field of the Invention

This invention relates to apparatus which apply electrical currents to the human body and are used to neutralize irritants such as venoms and other foreign substances which are introduced under the skin by the bite or sting of a variety of animals.

2. The Prior Art

A number of commonly encountered animals pose a threat to humans and domesticated animals due to their bites and/or stings. Numerous insects are capable of introducing or injecting various irritants under a victim's skin through a bite or a sting. Larger animals, such as snakes, can inject irritating or deadly venoms into their victims.

Electrical stimulation of the body for its useful effects is known in the art. Such stimulation has been carried out, for example, to speed bone growth and quicken healing of fractures, to provide relief of chronic pain, to simulate muscles and prevent muscle atrophy when nerves have been severed to the muscle, and to find the location of nerves during surgery.

It has recently been discovered that the application of an electrical current to the site of an insect or snake bite can reduce or eliminate the harmful effects of the introduced irritant. The previously proposed methods and apparatus for delivering an electrical current to the body to treat bites or stings have several problems and drawbacks.

Previously used apparatus have been crudely rigged or modified gasoline engine ignition coils or "stun gun" devices. Such devices are not intended for use in a therapeutic treatment and in the case of the stun gun are intended to give painful shocks in order to coerce a victim. Such Frankenstein-like devices and methods do not accurately control or measure the amount of current which is delivered to the body. Thus, the beneficial effects of such treatments cannot be maximized.

Further, such devices ignore the effect of skin resistance and electrode polarization on the treatment. When such effects are not considered, the treatment is much less effective. Moreover, such apparatus are often unwieldy and are not suitable for carrying on one's person or in a portable first aid kit. Still further, since the current applied to the victim is not controlled or measured, the treatments are often painful and victims often forego electrical stimulation therapy for less painful treatments.

In some cases, individuals are hyper-sensitive to insect bites or stings. Having a compact, portable device which could be carried everywhere and which would effectively treat insect bites could be a life saving advantage for hypersensitive persons. In addition to those who are hypersensitive to insect bites and stings, individuals traveling in areas where venomous snakes are common would welcome a device which could be easily carried and which would effectively treat any snake or insect bite immediately rather than having to hurriedly travel to a medical center and receive specific treatment for each particular kind of snake, spider, or insect bite.

In view of the forgoing, it would be an advance in the art to provide a compact apparatus for applying an electrical current to a site on the body in order to reduce or neutralize the effect of an irritant introduced into the body by a snake, spider, or insect bite.

BRIEF SUMMARY AND OBJECTS OF THE INVENTION

In view of the above described state of the art, the present invention seeks to realize the following objects and advantages.

It is a primary object of the present invention to provide an apparatus for applying an electric current to a subject and efficiently reducing the effect of an irritant which has been injected into the subject's body.

It is also an object of the present invention to provide an apparatus for applying an electric current to a subject for relieving the effects of an animal sting or bite which is compact, easily carried, and self contained.

It is another object of the present invention to provide an apparatus for treating a subject with an electric current for relieving the effects of an animal sting or bite which is relatively comfortable for the subject.

It is still another object of the present invention to provide an apparatus for applying an electric current to a subject for relieving the effects of an animal sting or bite wherein the current which is applied to the subject is controlled.

It is yet another object of the present invention to provide an apparatus for applying an electric current to a subject for relieving the effects of an animal sting or bite wherein the current which is applied to the subject is measured and displayed in real time.

It is another object of the present invention to provide an apparatus for applying an electric current to a subject for relieving the effects of an animal sting or bite wherein tissue damage due to the treatment is minimized.

It is also an object of the present invention to provide an apparatus for applying an electric current to a subject for relieving the effects of an animal sting or bite wherein the current which is applied to the subject can be adjusted to different levels to adapt for differing individuals and different parts of a subject's body.

These and other objects and advantages of the invention will become more fully apparent from the description and claims which follow, or may be learned by the practice of the invention.

The present invention is an apparatus for neutralizing, or reducing the effects of, irritants introduced into a subject's body by the sting or bite of an animal such as a snake, spider, or insect. Preferred embodiments of the apparatus include a self contained electrical power source which can be a battery, piezoelectric generator, or electromagnetic generator. Preferably, the apparatus is compact and can be easily carried into remote areas when engaging in activities such as backpacking.

A pair of electrodes are provided on the apparatus. The electrodes are adapted to make electrical contact with the subject's body at the site of a sting or bite. A means for generating a series of pulses is also included in the apparatus. The series of pulses are conveyed to the electrodes. In order for the treatment to be most effective, the pulses have a frequency from about 5 Hz to about 50 Hz and a duration from about 50 microseconds to about 50 milliseconds. Other preferred pulse durations are in the range from about 50 microseconds to about 250 milliseconds.

The apparatus also includes means for adjustably controlling the current delivered to the electrodes. By adjusting the frequency of the pulses, the length of the pulses (or duty cycle), and the current delivered by the pulses, the treatment can be most efficiently carried out. That is, relief from the bite or sting can be given to the subject with a minimum of discomfort due to the treatment itself. It is preferred that the current pulses delivered to the body be in the range from about 100 microamps to about 100 milliamps. Other preferred current ranges are from about 500 microamps to about 50 milliamps and from about 250 microamps to about 10 milliamps.

The apparatus also comprises a means for measuring the electrical charge (current multiplied by time) delivered to the body through the electrodes over a period wherein a plurality of pulses have been delivered to the body. A visual metering device is preferably included to give a real time indication of the current delivered to the subject.

In order to make the treatment most effective, the apparatus preferably comprises a means for making the pulses alternately positive and negative pulses wherein a substantially equal number of positive pulses and negative pulses are conveyed to the electrodes over the period of time which the pair of electrodes are in contact with the body. This reduces problems such as electrode polarization and tissue damage. The apparatus can further include a means for dispensing a conductive gel onto the electrodes so that the resistance at the electrode/skin interface is minimized.

BRIEF DESCRIPTION OF THE DRAWINGS

In order to better appreciate how the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENT

Reference will now be made to the drawings wherein like structures will be provided with like reference designations.

Figure 1:
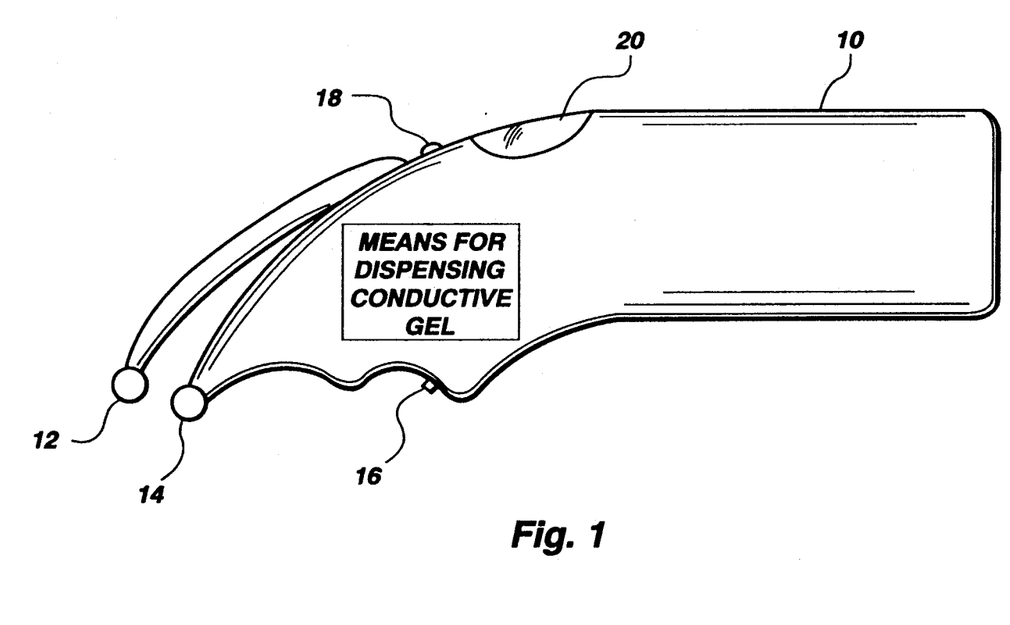
FIG. 1 represents a presently preferred embodiment of the present invention.

Reference will first be made to FIG. 1 which is a representation of a presently preferred embodiment of the present invention. In contrast to the previous methods and devices used apply an electric current to reduce the effect of a sting or a bite, embodiments of the present invention are small enough to be carried about on one's person. Desirably, the present invention is applied to the site of a sting or a bite immediately following the incident. The present invention allows the most effective treatment to occur, and discomfort to the subject minimized, by keeping the current flow through just the affected area of the body.

The embodiment of the present invention includes a case 10 which is conveniently held in one hand. Two electrodes 12 and 14 are also provided. The two electrodes 12 and 14 can be separated by anywhere from fractions of an inch to several inches. Desirably, only the site of the bite or sting will be subjected to the electric current. Treatment by the present invention subjects only the affected sting or bite area to the electric current. Thus, the treatment by the present invention is much less painful to endure, if any pain at all results from the treatment, than the previously used apparatus. Such previously used apparatuses employ the naturally occurring current paths to ground in a subject's body (i.e. legs). Because much less of the subjects body is involved in the treatment, use of the present invention is much less uncomfortable. It is within the scope of the present invention to provide a means for altering the spacing between the electrodes 12 and 14 so that the path of the current can be limited to just the immediate area of the sting or bite.

It is also within the scope of the present invention to include a means for dispensing a conductive electrolyte gel onto the electrode and/or the skin of the subject. For example, a hollow electrode in cooperation with a manually operated squeeze dispenser of gel can be included to function as a means for dispensing the gel. The conductive gel reduces the resistance found at the electrode/skin interface.

The embodiment illustrated in FIG. 1 is also provided with an activation switch 18 which is actuated in order to operate the embodiment. Furthermore, the shape of case 10 can be varied in accordance with the particular application for which the embodiment is intended. For example, a compact embodiment which is to be carried by a lone person and intended for self-administration should have a case shape making it easy for the subject to reach any part of his body while operating the necessary controls. Embodiments intended for other applications, such as use by paramedics and other health care professionals, can include other features and arrangements.

Also represented in FIG. 1 is a meter 20 which indicates, as will be explained shortly, the amount of charge which has passed through the tissue between the electrodes 12 and 14. A reset switch 16 is provided to reset the meter 20 back to zero. The meter 20 can be an electro-mechanical meter movement, a digital display, or some other visual or audio display which indicates to the user the amount of current which has passed through the electrodes.

Figure 2:
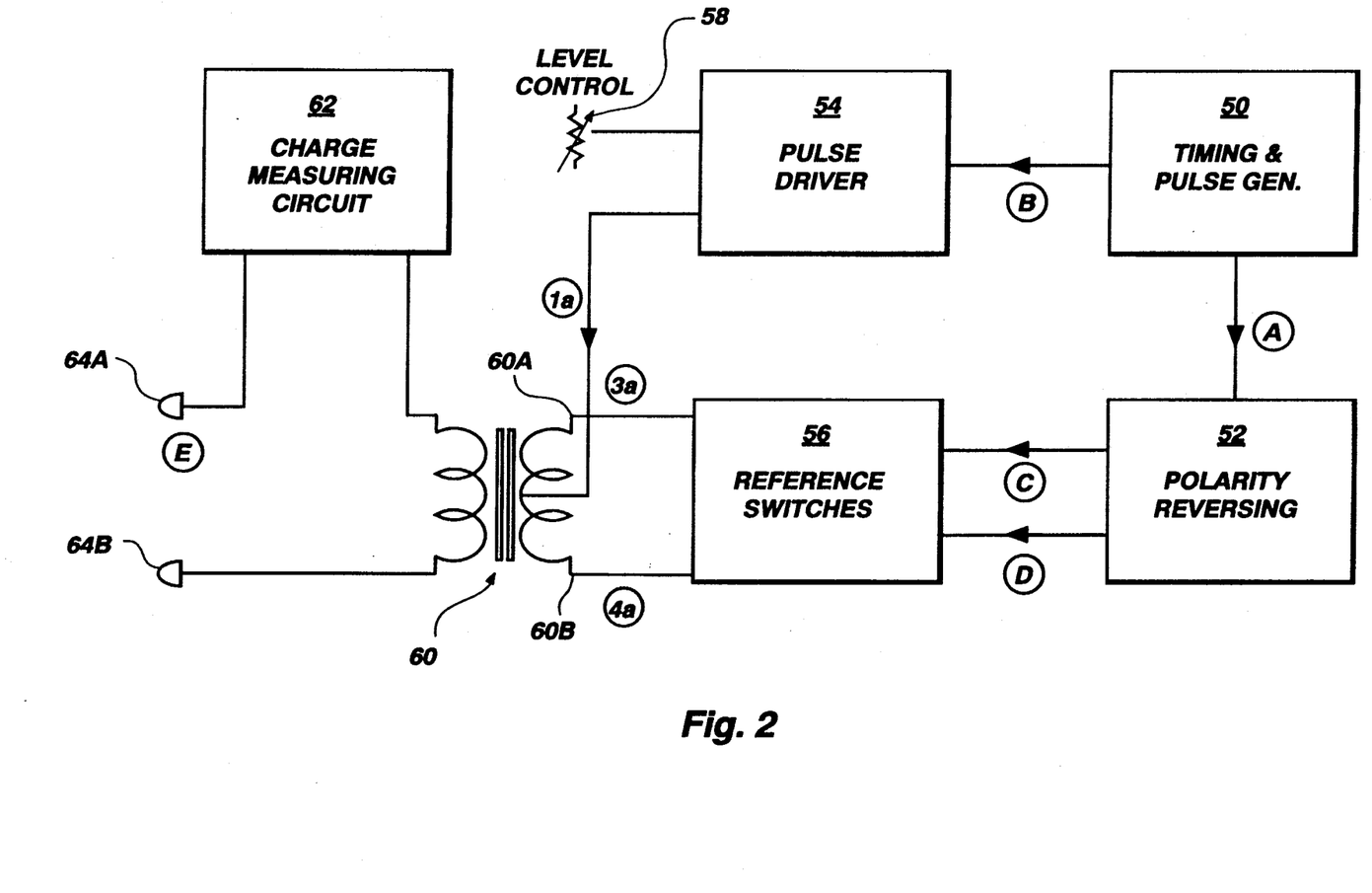
FIG. 2 is a block diagram representing the electrical components included in the presently preferred embodiment.
Figure 2A:
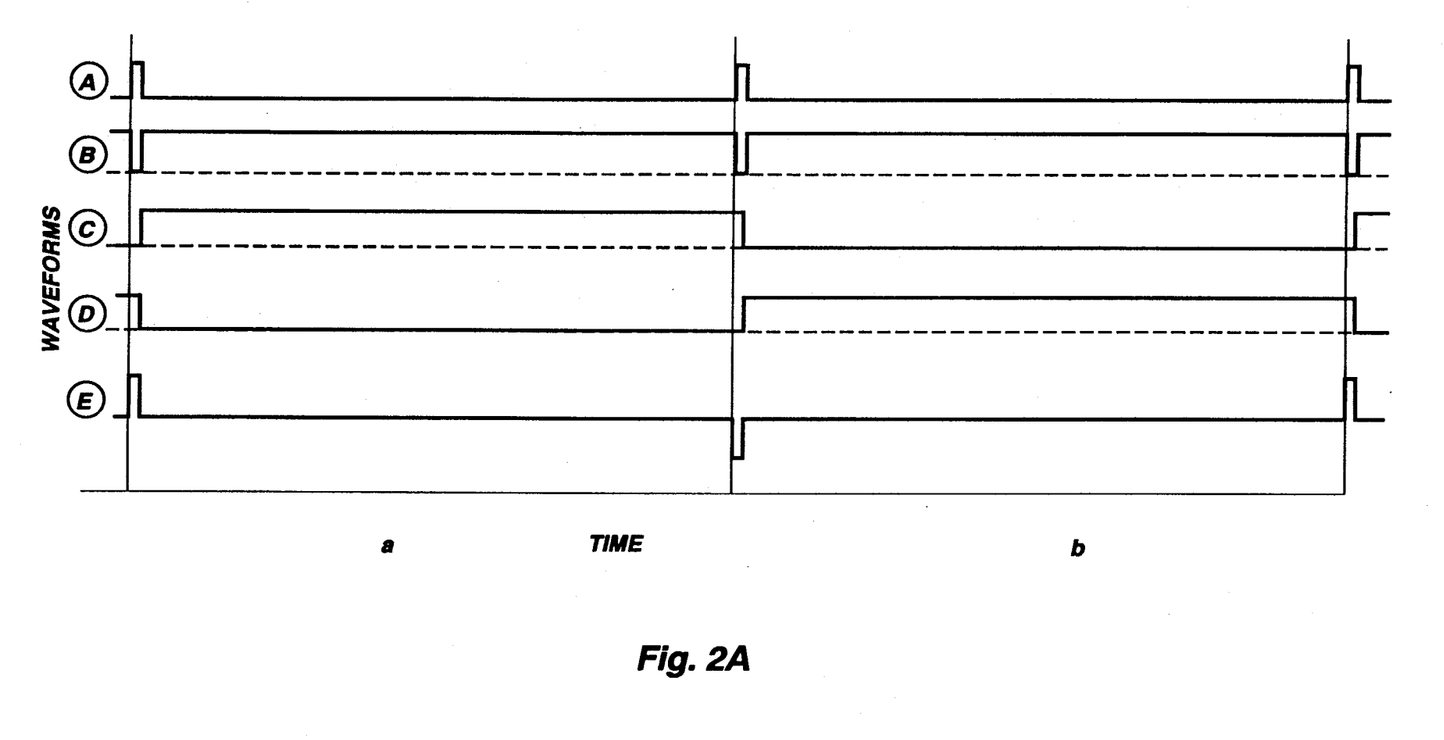
FIG. 2A is a timing diagram showing the waveforms output from the components represented in the block diagram of FIG. 2.

Reference will next be made to FIG. 2 which is a block diagram of the preferred embodiment of the present invention and to FIG. 2A which is a waveform diagram providing idealized representations of the waveforms referenced in the block diagram of FIG. 2. The represented embodiment is primarily comprised of five circuits and an output transformer 60 which functions as what is commonly referred to as a step-up transformer. The circuits include: a timing and pulse generating circuit 50; polarity reversing circuit 52; pulse driver circuit 54; reference switches circuit 56; and charge measuring circuit 62.

Also provided in the presently preferred embodiments of the present invention is a power source. Desirably, the power source can be a battery for self contained operation but the embodiment can derive its energy from any number of sources. For example, it is within the scope of the present invention to include a manually operable piezoelectric or electromagnetic generator to provide a source of energy.

The timing and pulse generation circuit 50 sets the timing (pulse repetition rate) and the pulse size generation (output pulse width). Thus, this circuit provides pulses of pre-determined width at a specific rate. The output from the timing and pulse generation circuit 50 provides two functions: the generation of a pulse which is conveyed to the pulse driver circuit 54 and a trigger which is conveyed to the polarity reversing circuit 52. The trigger for the polarity reversing circuit 52 is the negative going edge of the positive pulse represented in Waveform A of FIG. 2A and is used to change state in the polarity reversing circuit 52. The pulse output is shown as a negative going signal in Waveform B which becomes inverted in the pulse driver circuit 54.

It is preferred that the pulse which is output be of relatively short duration. For example, a pulse between 50 microseconds and 50 milliseconds is preferred, with a pulse in the range from about 500 microseconds to about 2 milliseconds being most preferred. Moreover, the duty cycle of the waveform is preferably relatively low, e.g., from about 1% to about 15% with the most desirable range being from about 2% to about 5%. The short pulse duration and low duty cycle maintains the subject's healthy tissue exposure to the current at relatively low levels. The rate at which the pulses are applied to the subject can also be expressed as cycles per second, or Hz, with a preferred value being from about 5 Hz to about 50 Hz. Other values for the pulse duration and the duty cycle can also be used within the scope of the present invention.

The polarity reversing circuit 52 comprises a multivibrator circuit. The polarity reversing circuit is a bi-stable circuit that drives the reference switches circuit 56. The primary function of polarity reversing circuit 52 is to cause every other pulse which is output from the embodiment to be of opposite polarity. The reference switches circuit 56 preferably comprises a pair of transistors whose function is to change the reference of the output transformer's 60 primary winding thereby changing the output pulse polarity.

Significantly, the output transformer 60 is provided with a center tap into which is fed the output from the pulse driver 54. This is different than the conventional wisdom in the art which teaches that the center tap should be connected to the ground reference. In the described embodiment, the legs 60A and 60B of the output transformer primary winding are alternately referenced to ground by the reference switches circuit 56. This provides an elegant method of reversing the polarity of the output pulse. Waveforms C and D illustrated in FIG. 2A represent the waveforms which are input to and output from the reference switches circuit 56. The waveforms illustrated in FIG. 2A are depicted in two time periods, a and b, to clearly show the bipolar nature of the waveforms.

By providing a bi-polar output from the embodiment, the undesirable effects of electrode polarization are minimized or altogether avoided. Also, the utilization of a bi-polar output, whether every other pulse is of opposite polarity or the number of positive and negative pulses over a period of time are substantially equal, reduces the degradation of healthy tissue which is subjected to the treatment.

Referring still to FIG. 2, the pulse driver circuit 54 inverts and boosts the power level of the pulse generated by the timing and pulse generator circuit 50. The Waveform A of FIG. 2A describes the output of the pulse driver circuit 54. It will be appreciated that the waveforms of FIG. 2A are not to scale and provide an idealized, not actual, representation of the waveforms. The output of the pulse driver circuit drives the output transformer 60. The pulse which is conveyed to the electrodes 64A and 64B and thus to the subject is represented by Waveform E in FIG. 2A.

The size of the pulses which are output from the embodiment are adjusted by a level control 58. Advantageously, the level control 58 allows the size of the pulses to be adjusted according to the sensitivity of the subject and the seriousness of the bite or sting. For example, the level control can be used to reduce the size of the pulses for children or for use on sensitive parts of the subject's body.

Figure 2B:
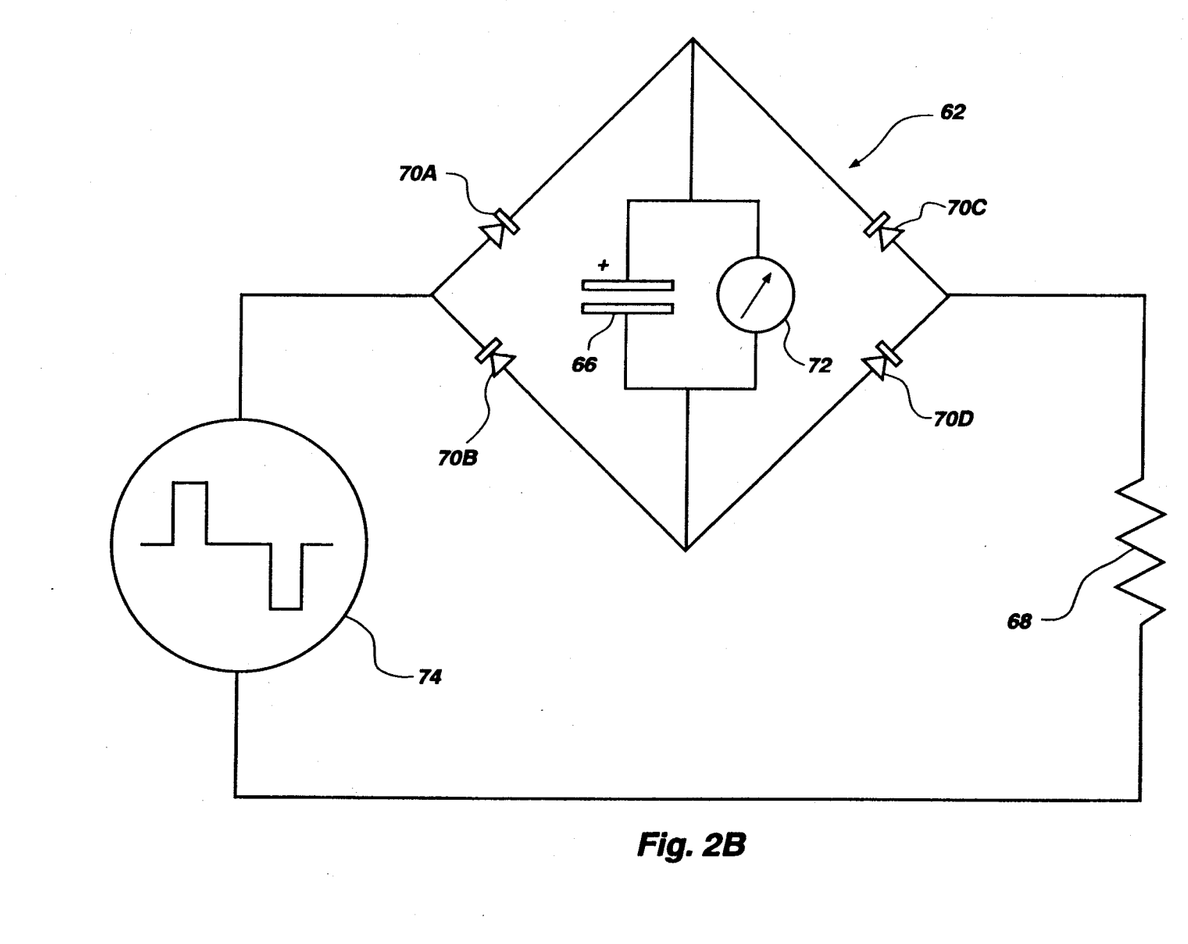
FIG. 2B is a diagram showing the arrangement of the preferred charge measuring circuit.

Still referring to FIG. 2, the charge measuring circuit 62 provides the important function of measuring, in real time, the charge which has passed through the electrode 64A and thus also the charge which has passed through the subject. In FIG. 2B, a simplified diagram showing the preferred structure for the charge measuring circuit 62 is provided.

As represented in FIG. 2B, a complete current loop is formed by the components which generate a pulse (represented by generator 74) which is applied to a subject (represented by load resistor 68) and by the charge measuring circuit generally represented at 62. Note that every other pulse which is generated is inverted o of opposite polarity. As each pulse is generated, electrons move about the loop.

The charge measuring circuit 62 operates by placing a capacitor 66 in series with the load 68 (which is principally the resistance of the subject's tissue between the electrodes 64A and 64B in FIG. 2) and then observing the voltage accumulate across the capacitor 66 while applying current to the load. Since the output of the embodiment is bipolar, the capacitor 66 is connected "inside" a bridge rectifier
comprising diodes 70A–70D as illustrated in FIG. 2B. The diodes of the bride rectifier "steer" successive pulses so that the capacitor 66 always sees the same pulse polarity. This allows the capacitor to accumulate a small "step charge" with each pulse. Evidence of these incremental charges is seen as voltage across the capacitor 66.

With the capacitor 66 connected as shown in FIG. 2B, the current applied to the capacitor is always the same sign. A meter 72 is included to measure the voltage present across the capacitor 66 which reflects the accumulated charge of the capacitor 66 and the total current through the subject. Other devices, such as a liquid crystal bar graph, can be used as a metering device.

Because the capacitor 66 is effectively in series with the load 68, it can be said that electron movement in the load 68 is reflected by electron movement in the capacitor. In other words, the capacitor "totals up" the electron movement, even though the movement of electrons in the load are continually reversing.

The value of the capacitor 66 is selected so that the accumulated voltage is small and does not significantly effect the current delivered to the load 68. The charge measuring circuit is virtually transparent to the generator 74 and the load 68. Importantly, the generator 74 must have a high output impedance, for example, by being configured to operate in a current mode.

Figure 3:
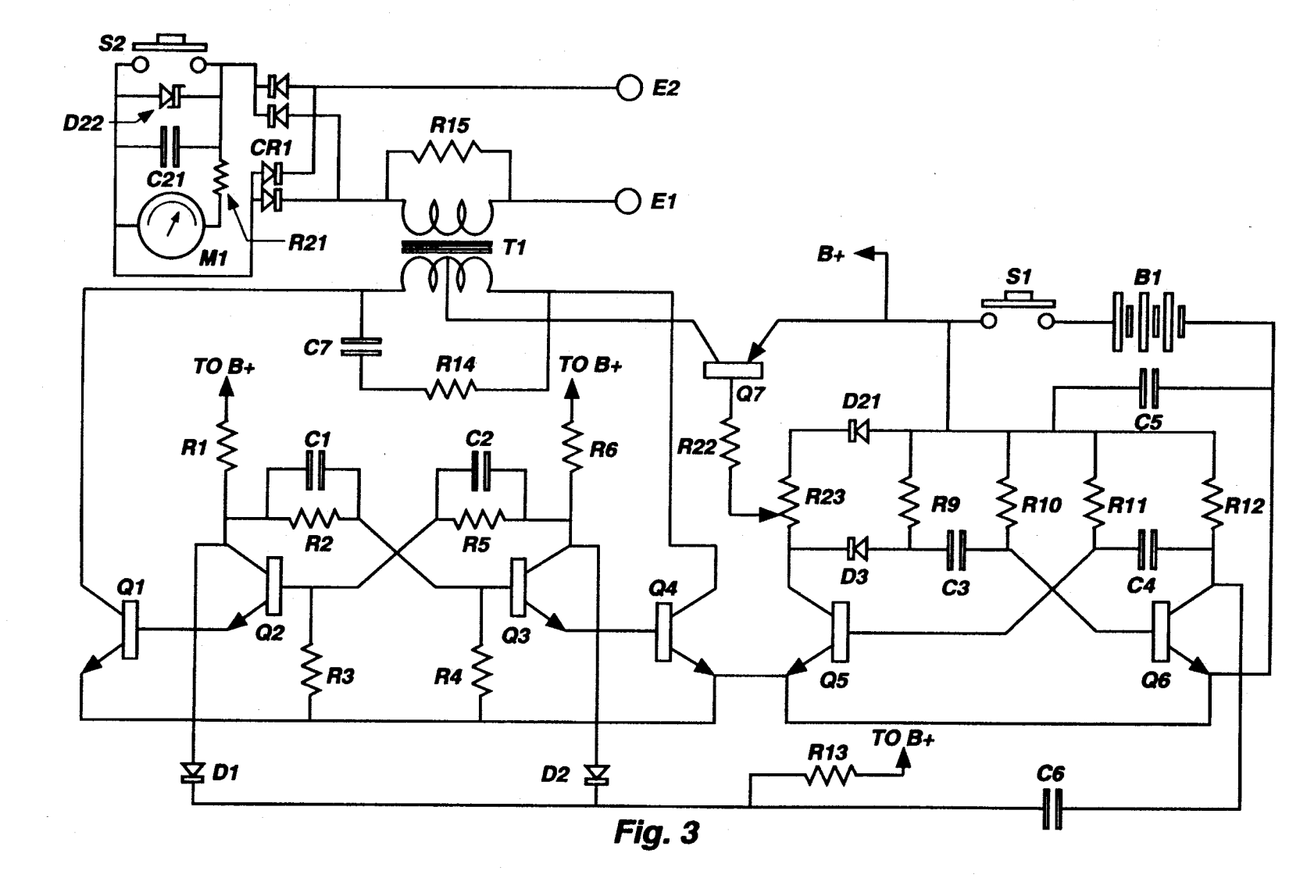
FIG. 3 is a detailed schematic diagram of the presently preferred embodiment.

Reference will next be made to FIG. 3 which is a detailed schematic diagram of the presently preferred embodiment. It is to be understood that the present invention can be embodied in many arrangements other than that specifically described herein. For example, many of the functions carried out by the components represented in FIG. 3 can be incorporated into one or more integrated circuits. Moreover, the operating parameters of other embodiments of the present invention may be different from that of the embodiment illustrated in FIG. 3.

In order to maintain the clarity of the detailed schematic of FIG. 3, the reference designations which are commonly found in the art in such schematic diagrams have been retained.

Referring still to FIG. 3, transistors Q5 and Q6 form part of a stable free-running multi-vibrator circuit with timing components comprising resistors R10 and R11 in cooperation with capacitors C3 and C4, respectively. Transistor Q5 provides signal drive via potentiometer R23, which functions as a level control, to transistor Q7, which functions as a pulse driver, while diode D3 provides rapid decay of pulse trailing edge. Diode D21 functions to compensate for the offset of the base-emitter junction of Q7 and produces the aperture compentsation.

Diode D3 isolate the drive signal from the effects of recharging timing capacitor C3 through resistor R9. Resistor R12 provides a load for transistor Q6 and charges capacitor C4. A signal is also conveyed from the collector of transistor Q6 via capacitor C6 to coupling diodes D1 and D2. These diodes provide a "turn-off" signal to whichever of transistors Q2 or Q3 is turned on. A resistor R13 provides a discharge path for the capacitor C6.

Transistors Q2 and Q3 form part of a bi-stable multi-vibrator circuit, i.e., two stable states. Resistors R1 and R6 function as loads for the collectors of transistors Q2 and Q3, while resistors R2 and R5 function as base drive resistors. Capacitors C1 and C2 provide necessary delay time during triggering of state changes. An output is taken from the emitters of transistors Q2 and Q3. Resistors R3 and R4 ensure that transistors Q2 and Q3, whichever transistor which is in the off state and its accompanying switch, are not leaking current into the primary winding of transformer T1.

Still referring to FIG. 3, transistors Q1 and Q4 function as switches which alternately ground the legs of the primary winding of transformer T1. The alternative grounding of the legs of the primary winding of transformer T1 causes the drive pulses output from transistor Q7 to result in a bi-polar output from the secondary winding of the transformer T1. The input pulse to transformer T1 is provided by the collector of transistor Q7. A resistor R15 provides a minimum load to the driving circuitry in order to prevent excessive voltage in the secondary winding of the transformer T1.

Also represented in FIG. 3 is a battery B1. A push-button switch S1 starts the apparatus into operation. A capacitor C5 functions to provide dynamic impedance lowering of the battery B1 by supplying much of the current required during the output pulse and then recharging in the time between output pulses. It will be appreciated that the battery B1 may be replaced with other power sources. The B+designations provided in FIG. 3 illustrate a common battery connections.

The current passed through the electrodes is measured by placing a capacitor C21 in series with the load across the electrodes E1 and E2 and then observing the voltage across the capacitor C21 while current is applied to the subject. Since the output is bi-polar, the capacitor C21 is connected inside a bridge rectifier CR1 so the current directed through the capacitor 21 is always of the same polarity. A resistor R21 converts current meter M1 into a voltage sensitive indicator which monitors and/or measures the accumulated charge found on the capacitor C21. The push-button switch S2 is provided to discharge the capacitor and reset the charge measurement reading of the meter M1 for a successive application of current to the subject if needed. A diode D22 is provided to prevent overcharge of the capacitor and additionally, to ensure that the apparatus will still function properly even if the user fails to discharge the capacitor.

As indicated earlier, embodiments of the present invention can be made compact and easy to operate so that they can be adapted for use by individuals in remote locations or by fully equipped medical personnel. After the subject has experienced a sting or bite, the apparatus is applied to the site. It is desirable that a small amount of conductive electrolyte gel be placed on each electrode to reduce the resistance of the skin/electrode interface. Desirably, precautions should be taken not to smear the entire area of the injury with the conductive electrolyte gel as it will impair the effectiveness of the treatment. Getting the gel too widely dispersed can create a current path between the electrodes and cause most of the applied current to travel on the surface of the subject's skin rather than through the underlying tissue where the treatment will be much more effective.

The apparatus's electrodes are brought into contact with the affected site. Desirably, one electrode is placed directly on the location of the puncture of the skin and the other electrode is brought into contact at a convenient adjacent location. The apparatus is then activated (by actuating S1 in FIG. 3). The treatment should be timed and a means for timing the treatment can be included in the apparatus of the present invention. For example, an aural or visual indication of the passage of one or two minutes of treatment can be provided. Longer treatments will be most effective for more serious bites and stings.

It may be desirable to provide numerous separate applications. The most common indication of needing additional treatment is recurrence of discomfort at the site of the sting or bite. It is believed that there is no significant risk due to exposure to the treatment and thus over application of the treatment is not a great concern. Still, long applications may result in some discomfort so care should be taken.

In view of the foregoing, it will be appreciated that the present invention provides an apparatus for applying an electric current to a subject and efficiently reducing the effect of an irritant which has been introduced into the subject's body. The present invention also provides an apparatus for applying an electric current to a subject for relieving the effects of an animal sting or bite which is compact, easily carried, self-contained, and which is relatively comfortable for the subject.

The present invention further provides an apparatus for applying an electric current to a subject for relieving the effects of an animal sting or bite wherein he current which is applied to the subject is controlled, measured in real time, and wherein collateral tissue damage is minimized. The invention also provides an apparatus for applying an electric current to a subject for relieving the effects of an animal sting or bite wherein the current can be adjusted to different levels to adapt for differing individuals and different parts of a subject's body.

Provided below in Table A is a list of the components represented in FIG. 3 and providing preferred component values.

TABLE A

| Reference Designation | Value |
| --- | --- |
| Q1 | Transistor 2N4401 |
| Q2 | Transistor 2N4124 |
| Q3 | Transistor 2N4124 |
| Q4 | Transistor 2N4401 |
| Q5 | Transistor 2N4124 |
| Q6 | Transistor 2N4124 |
| Q7 | Transistor 2N4403 |
| D1 | Diode |
| D2 | Diode |
| D3 | Diode |
| D21 | Diode |
| D22 | Diode |
| C1 | Capacitor .033 uf |
| C2 | Capacitor .033 uf |
| C3 | Capacitor .0047 uf |
| C4 | Capacitor 0.1 uf |
| C5 | Capacitor 15 uf Capacitor 16 v |
| C6 | Capacitor 470 pf |
| C7 | Capacitor 470 pf |
| C21 | |
| R1 | Resistor 3.9K |
| R2 | Resistor 130K |
| R3 | Resistor 240K |
| R4 | Resistor 240K |
| R5 | Resistor 130K |
| R6 | Resistor 3.9K |
| R9 | Resistor 39K |
| R10 | Resistor 160K |
| R11 | Resistor 470K |
| R12 | Resistor 1.5K |
| R13 | Resistor 43K |
| R14 | Resistor 680 |
| R15 | Resistor 100K |
| R21 | Resistor 130K |
| R22 | Resistor 3.3K |
| R23 | Potentiometer 2.5K |
| S1 | Switch |
| S2 | Switch |
| T1 | Transformer, Center- tap, step-up |
| B1 | Battery 9 volt |
| CR1 | Bridge rectifier |

The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United State Letters Patent is:

1. An apparatus for neutralizing irritants introduced into a subject's body by an animal, the apparatus comprising:
   a self contained electrical power source;
   a pair of electrodes adapted for contact with the body;
   means connected to said power source for generating a series of pulses to the electrodes for delivering an electrical current to the body, the pulses having a frequency from about 5 Hz to about 50 Hz and a duration from about 50 microseconds to about 50 milliseconds;
   means for adjustably controlling the current delivered to the body being in the range from about 100 microamps to about 100 milliamps; and
   means for measuring an accumulated charge delivered to the body through the electrodes over a period of time wherein a plurality of pulses have been delivered to the body.

2. An apparatus for neutralizing irritants introduced into a subject's body by an animal as defined in claim 1 wherein the electrical power source comprises a manually operable piezoelectric generator.

3. An apparatus for neutralizing irritants introduced into a subject's body by an animal as defined in claim 1 wherein the means for adjustably controlling the current delivered to the electrodes provides a current in the range from about 250 microamps to about 10 milliamps.

4. An apparatus for neutralizing irritants introduced into a subject's body by an animal as defined in claim 1 wherein the electrical power source comprises a manually operable electromagnetic generator.

5. An apparatus for neutralizing irritants introduced into a subject's body by an animal as defined in claim 1 wherein the electrical power source comprises a battery.

6. An apparatus for neutralizing irritants introduced into a subject's body by an animal as defined in claim 1 wherein the means for generating a series of pulses comprises a timing and pulse generating circuit and a pulse driver circuit.

7. An apparatus for neutralizing irritants introduced into a subject's body by an animal as defined in claim 1 further comprising means for making the pulses both positive pulses and negative pulses wherein a substantially equal number of positive pulses and negative pulses are conveyed to the electrodes over the period of time wherein the pair of electrodes are in contact with the body.

8. An apparatus for neutralizing irritants introduced into a subject's body by an animal as defined in claim 7 wherein the means for generating comprises an output step-up transformer.

9. An apparatus for neutralizing irritants introduced into a subject's body by an animal as defined in claim 7 wherein the means for generating a series of pulses comprises means for alternately generating positive and negative pulses, the charge transferred to the body during the positive pulses being substantially equal to the charge transferred to the body during the negative pulses.

10. An apparatus for neutralizing irritants introduced into a subject's body by an animal as defined in claim further comprising means for dispensing a conductive gel onto the electrodes.

11. An apparatus for neutralizing irritants introduced into a subject's body by an animal as defined in claim 1 wherein the means for measuring the accumulate charge comprises a measuring device connected in series with the electrode wherein the measuring device comprises a voltage measuring device connected in parallel with a capacitor, the capacitor being connected so that it charges as the number of electrons flowing through the pair of electrodes increases.

12. An apparatus for neutralizing irritants introduced into a subject's body by an animal as defined in claim 11 wherein the means for measuring the current further comprises a bridge rectifier circuit and a meter connected within the rectifier circuit.

13. An apparatus for neutralizing irritants introduced into a subject's body by an animal as defined in claim wherein the means for adjustably controlling the current comprises a pulse driver circuit and a level control connected to the pulse driver circuit.

14. An apparatus for reducing the effect of irritants injected into a subject's body such as by the bite, or sting of an animal, the apparatus comprising:
a self-contained electrical power source;
a pair of electrodes adapted for contact with the body;
means connected to said power source for generating a series of pulses to the electrodes, the pulses comprising a substantially equal number of positive pulses and negative pulses over the period of time when the pair of electrodes are in contact with the body;
means for controlling current delivered to the electrodes, the current delivered to the electrodes and to the body being maintained in the range from about 500 microamps to about 50 milliamps in order to relieve the effects of the irritant; and
means for measuring the accumulated charge delivered to the body through the electrodes over a period of time wherein a plurality of pulses have been delivered to the body.

15. An apparatus for reducing the effect of irritants injected into a subject's body such as by the bite, or sting of an animal as defined in claim 14 wherein the electrical power source comprises a battery.

16. An apparatus for reducing the effect of irritants injected into a subject's body such as by the bite, or sting of an animal as defined in claim 15 wherein the means for generating comprises means for generating a series of pulses which are conveyed to the electrodes, the pulses having a frequency from about 5 Hz to about 50 Hz and a duration from about 50 microseconds to about 50 milliseconds.

17. An apparatus for reducing the effect of irritants injected into a subject's body such as by the bite, or sting of an animal as defined in claim 15 wherein the means for generating a series of pulses comprises:
a timing and pulse generating circuit;
a pulse driver circuit; and
a step-up output transformer.

18. An apparatus for reducing the effect of irritants injected into a subject's body such as by the bite, or sting of an animal as defined in claim 14 wherein means for generating a series of pulses comprises means for generating positive and negative pulses which are alternately applied to the electrodes.

19. An apparatus for reducing the effect of irritants injected into a subject's body such as by the bite, or sting of an animal as defined in claim 14 wherein means for measuring comprises means for visually displaying the accumulated charge transferred to the subject's body.

20. An apparatus for reducing the effect of irritants injected into a subject's body such as by the bite, or sting of an animal as defined in claim 14 wherein means for controlling the current comprises means for adjustably controlling the current delivered to the electrodes, the current delivered to the electrodes and to the body being in the range from about 500 microamps to a bout 10 milliamps.

21. A method for treating the site where an irritant has been introduced into a body by the sting or bite of an animal, the apparatus comprising:
applying a first electrode substantially at the site of the sting or bite;
applying a second electrode at a location substantially adjacent to the site of the sting or bite;
generating a series of electrical pulses which are conveyed to the electrodes, the pulses having a frequency not greater than substantially 50 Hz and a duration from about 50 microseconds to about 250 milliseconds, the pulses comprising a substantially equal number of positive pulses and negative pulses over the period of time during which the electrodes are in contact with the body;
measuring a charge transferred to the body through the electrodes over a period of time wherein a plurality of pulses have been delivered to the body; and
visually displaying an indication of the charge transferred to the body.

* * * * *

UNITED STATES PATENT AND TRADEMARK OFFICE
CERTIFICATE OF CORRECTION

PATENT NO. : 5,235,990
DATED : August 17, 1993
INVENTOR(S) : Robert H. Dempsey

It is certified that error appears in the above-indentified patent and that said Letters Patent is hereby corrected as shown below:

On the title page, item (76) Inventors, should read:
--Robert H. Dempsey--.

Signed and Sealed this

Twenty-eighth Day of June, 1994

Attest:

BRUCE LEHMAN

*Attesting Officer*   *Commissioner of Patents and Trademarks*